US010123948B2

(12) United States Patent
Klee et al.

(10) Patent No.: US 10,123,948 B2
(45) Date of Patent: Nov. 13, 2018

(54) DENTAL COMPOSITION

(71) Applicant: DENTSPLY International Inc., York, PA (US)

(72) Inventors: Joachim E Klee, Radolfzell (DE); Helmut Ritter, Wuppertal (DE); Sven Pohle, Constance (DE); Oliver Elsner, Kussaberg (DE); Mareike Bardts, Dusseldorf (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/011,021

(22) Filed: Jan. 29, 2016

(65) Prior Publication Data
US 2016/0143818 A1 May 26, 2016

Related U.S. Application Data

(63) Continuation of application No. 14/710,927, filed on May 13, 2015, now abandoned, which is a continuation-in-part of application No. 13/512,769, filed as application No. PCT/EP2010/007435 on Dec. 7, 2010, now abandoned.

(30) Foreign Application Priority Data

Dec. 15, 2009 (EP) ..................... 09015541

(51) Int. Cl.
*A61K 6/083* (2006.01)
*A61K 6/00* (2006.01)
*C08F 218/06* (2006.01)
*C08F 265/02* (2006.01)
*C08F 267/04* (2006.01)

(52) U.S. Cl.
CPC .......... *A61K 6/0835* (2013.01); *A61K 6/0038* (2013.01); *A61K 6/083* (2013.01); *C08F 218/06* (2013.01); *C08F 265/02* (2013.01); *C08F 267/04* (2013.01)

(58) Field of Classification Search
CPC ...................................... A61K 6/083
See application file for complete search history.

(56) References Cited

U.S. PATENT DOCUMENTS 6,476,092 B1 * 11/2002 Kunita ................. B41C 1/1008
430/286.1

* cited by examiner

*Primary Examiner* — Michael Pepitone
(74) *Attorney, Agent, or Firm* — Sushma Chauhan; Douglas Hura; Leana Levin

(57) ABSTRACT

A dental cement hardened by a cement reaction involving the specific polymerizable polyacidic polymer and optionally additional crosslinkable groups, has reduced shrinkage and improved mechanical properties, in particular with regard to flexural strength and fracture toughness. Moreover, the specific polymerizable polyacidic polymer of the present invention contains a high number of acidic groups which is not reduced by the presence of polymerizable moieties, whereby water solubility of the uncured polymer is not impaired by the presence of the polymerizable moieties.

11 Claims, No Drawings

DENTAL COMPOSITION

CROSS-REFERENCE TO RELATED APPLICATIONS

This application is a continuation application of U.S. patent application Ser. No. 14/710,927, filed May 13, 2015 (now abandoned), which a continuation in part application of U.S. patent application Ser. No. 13/512,769, filed May 30, 2012 (now abandoned), which is an national stage application of PCT/EP2010/007435, filed Dec. 7, 2010, which claims priority to European Patent Application No. 09015541.7, filed Dec. 15, 2009.

FIELD OF THE INVENTION

The present invention relates to a dental cement composition comprising a polymerizable polyacidic polymer having specific repeating units in the polymer backbone. Moreover, the present invention relates to a process for the preparation of the specific polymerizable polyacidic polymer. Finally, the present invention relates to the use of the specific polymerizable polyacidic polymer having specific repeating units in the polymer backbone and optionally additional crosslinkable groups, in a cement reaction with a reactive particulate glass.

A dental cement hardened by a cement reaction involving the specific polymerizable polyacidic polymer and optionally additional crosslinkable groups, has reduced shrinkage and improved mechanical properties, in particular with regard to flexural strength and fracture toughness. Moreover, the specific polymerizable polyacidic polymer of the present invention contains a high number of acidic groups which is not reduced by the presence of polymerizable moieties, whereby water solubility of the uncured polymer is not impaired by the presence of the polymerizable moieties.

BACKGROUND TO THE INVENTION

Conventional glass ionomer cements generally contain a powder component containing aluminosilicate, and a liquid component usually containing an aqueous mixture containing a polymer comprising acidic groups such as polyacrylic acid, polymaleic acid, polyitaconic acid, or a copolymer of at least two of these acids, cf. "New Aspects of the Setting of Glass-ionomer Cements," Wasson et al., Journal of Dental Research; Vol. 72, No. 2, February, 1993; pages 481-483. The most common polymers comprising acidic groups are derived from polyacrylic acid or copolymers of acrylic and itaconic acid (S. Crisp), acrylic acid and maleic acid.

In glass ionomer cements, the primary reactions which cause the glass ionomer cement to harden is crosslinking based on ionic forces between metal ions released from the glass and the polymer comprising acidic groups. Moreover, the acids of the glass ionomer cement partially dilute metal cations from the glass structure during setting so that ionic carboxylates of metal cations may be formed during the setting process.

Glass ionomers used as dental restoratives have advantages over conventional resin containing composites for several reasons. For example, glass ionomers are tolerant to application on wet surfaces, have low shrinkage and are self-adhesive. Since glass ionomers contain polymers rather than monomers, there is no risk of acrylic monomers leaching out, which can lead to sensitization and allergic reactions. Furthermore, glass ionomers bond chemically to dental hard tissues, and may also provide a beneficial level of fluoride release, which helps to prevent recurrent caries. Accordingly, ionomer cements are widely used in the dental field for filling of a cavity, cementing of crowns, inlays, bridges, or orthodontic bands, lining of a cavity, sealing of a root canal, core construction, and preventive sealing.

A key weakness of commercial glass ionomers, however, is their low flexural strength manifesting itself as an undesirable brittleness, which may lead to fracture at the edges of a restoration and, in the worst case, to bulk fracture of a restoration. Therefore, the restorative application of ionomer cements in posterior teeth is usually limited to non-stress bearing areas. ionomer cement materials continue to have significant limitations for use in permanent posterior restorations, particularly with regard to large restorations.

In order to improve the mechanical properties especially flexural strength and fracture toughness, numerous investigation were carried out, such as the use of amino acid modified polymers (Z. Ouyang, S. K. Sneckberger, E. C. Kao, B. M. Culbertson, P. W. Jagodzinski, Appl. Spectros 53 (1999) 297-301; B. M. Culbertson, D. Xie, A. Thakur, J. Macromol. Sci. Pure Appl. Chem. A 36 (1999) 681-96), application of water soluble copolymers using poly(N-vinylpyrrolidone) (D. Xie, B. M. Culbertson, G. J. Wang, J. Macromol. Sci. Pure Appl. Chem. A 35 (1998) 54761), use of polyacids with narrow molecular weight distribution (DE 100 58 829) and branched polyacids (DE 100 58 830). Further polyacids having a limited molecular mass ranging from 20,000 to 50,000 Da (EP 0 797 975) and 1,000 to 50,000 Da (WO 02/41845) were proposed. A further approach was the application of spherical ionomer particles (WO 00/05182).

Resin-modified glass-ionomer cements were introduced with an aim of overcoming the problems associated with the tendency towards brittle fracture of conventional glass-ionomer, while still retaining advantages such as fluoride release and adhesion (EP 0323120, U.S. Pat. No. 4,872,936 and U.S. Pat. No. 5,154,762). Accordingly, it was suggested to replace some of the water in a conventional glass-ionomer cement with a hydrophilic monomer or to modify the polymeric acid so that some of the acid groups were replaced with polymerizable moieties, so that the polymeric acid could also take part in a polymerization reaction.

Moreover, in order to address the problem of improving the mechanical properties of ionomer cement materials, U.S. Pat. No. 5,369,142 suggests the use of a specific acidic component, namely copolymers of acryloyl or methacryloyl derivatives of amino acids with acrylic acid or methacrylic acid. WO-A 02/062861 discloses polymer compositions for use in glass ionomer dental restoratives having improved resistance to bending and resistance to twisting, whereby the polymers are formed from at least two specific polymers. WO-A 03/061606 discloses ionomer cements containing amino acids improving the mechanical properties.

US 2002/0010227 discloses light-curable acid containing polymers in aqueous solution, which are obtainable by reacting polymers having reactive carboxylic acid groups with a methacrylated oxazoline or oxazine. WO03/011232 discloses resin-modified glass ionomer cements comprising a polymer having a plurality of acidic moieties and a plurality of polymerizable vinyl groups. The introduction of polymerizable moieties into a polyacrylic acid according to the prior art as set out in US 2002/0010227 or WO03/011232 means that water solubility of the polyacrylic acid deteriorates, which is not desirable in view of the viscosity and handling properties of a dental cement. Moreover, in case of WO03/011232, the leaching of HEMA from the cured composition and volume expansion of the cured cement represent major problems for an application in the dental field.

SUMMARY OF THE INVENTION

It is the problem of the present invention to provide novel and improved dental cement systems setting by a cement reaction whereby the cured cement has improved flexural strength and fracture toughness while at the same time the water solubility of the polymerizable polyacidic polymer is not deteriorated as compared to a corresponding polyacid polymer which does not contain the polymerizable moieties linked to an acidic group.

This problem is solved according to the invention with a dental cement composition comprising a polymerizable polyacidic polymer having repeating units in the polymer backbone, which are represented by the following formula (I), (II), and/or (III):

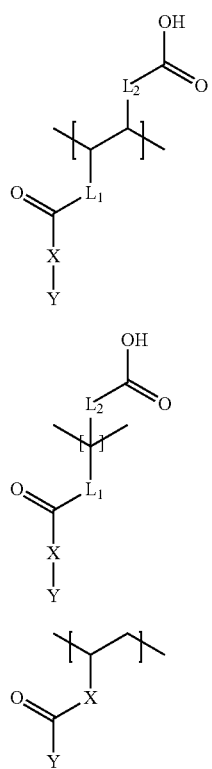

wherein
X
represents O, S, or NR', whereby R' represents a hydrogen atom or a straight or branched C1-C6 alkyl group, C3-C6 cycloalkyl group, or C4-C8 cycloalkylalkyl group,
Y
a group of the following formula (IV)

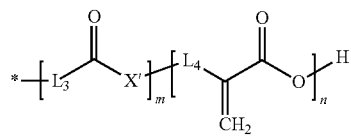

wherein each of L1, L2, L3 and L4,
which are independent from each other represents a single bond, a straight or branched C1-C6 alkylene group, a straight or branched C1-C6 alkenylene, or a straight or branched C1-C20 alkylene group which includes 1 to 8 atoms selected from oxygen and sulfur atoms,
X'
represents O, S, or NR", whereby R" represents a hydrogen atom or a straight or branched C1-C6 alkyl group, C3-C6 cycloalkyl group, or C4-C8 cycloalkylalkyl group,
m
is 0 to 3, and
n
is 1 to 3.

Furthermore, the present invention provides a process for preparing a polymerizable polyacidic polymer having repeating units in the polymer backbone which are represented by the following formula (I) and/or (II):

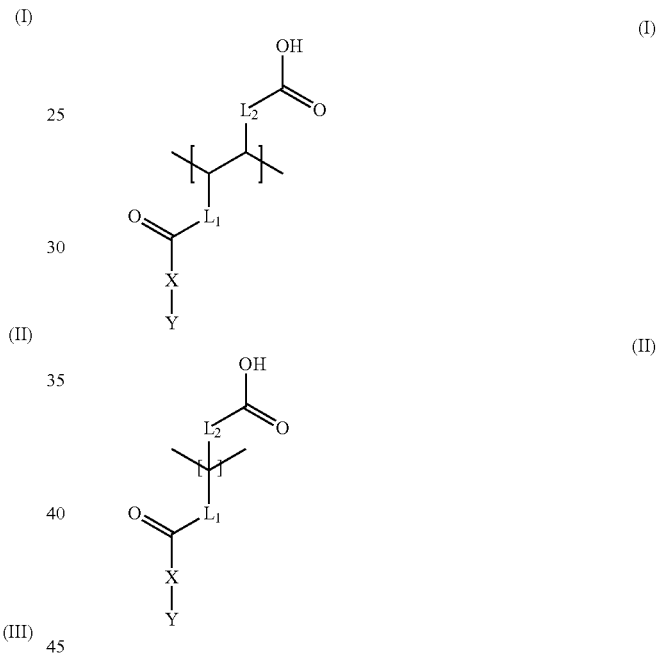

wherein
X
represents O, S, or NR', whereby R' represents a hydrogen atom or a straight or branched C1-C6 alkyl group, C3-C6 cycloalkyl group, or C4-C8 cycloalkylalkyl group,
Y
represents a group of the following formula (IV)

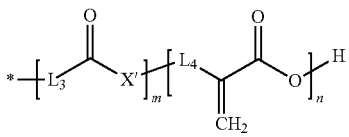

wherein each of L1, L2, L3 and L4,
which are independent from each other represents a single bond, a straight or branched C1-C6 alkylene group, a straight or branched C1-C6 alkenylene, or a straight or branched C1-C20 alkylene group which includes 1 to 8 atoms selected from oxygen and sulfur atoms, X'
represents O, S, or NR", whereby R" represents a hydrogen atom or a straight or branched C1-C6 alkyl group, C3-C6 cycloalkyl group, or C4-C8 cycloalkylalkyl group, m is 0 to 3, and
n
is 1 to 3,
said process comprising the steps of
(i) copolymerizing a mixture containing acrylic acid and one or more monomers selected from the group of maleic anhydride and itaconic anhydride, and
(ii) reacting the reaction product of (i) with HXY, wherein X and Y are as defined above.

Furthermore, the present invention also provides a process for preparing a polymerizable polyacidic polymer having repeating units in the polymer backbone which are represented by the following formula (III)
wherein

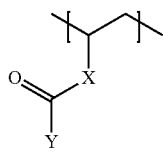 (III)

X
represents O, S, or NR', whereby R' represents a hydrogen atom or a straight or branched C1-C6 alkyl group, C3-C6 cycloalkyl group, or C4-C8 cycloalkylalkyl group,
Y
a group of the following formula (IV)

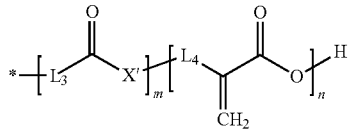

wherein each L3 and L4
which are independent from each other represents a single bond, a straight or branched C1-C6 alkylene group, a straight or branched C1-C6 alkenylene, or a straight or branched C1-C20 alkylene group which includes 1 to 8 atoms selected from oxygen and sulfur atoms,
X'
represents O, S, or NR", whereby R" represents a hydrogen atom or a straight or branched C1-C6 alkyl group, C3-C6 cycloalkyl group, or C4-C8 cycloalkylalkyl group,
m
is 0 to 3, and
n
is 1 to 3,
said process comprising the steps of reacting a carboxylic acid anhydride of YCOOH, wherein Y is as defined in claim 1, with a polymer or copolymer containing repeating units of the following formula (V):

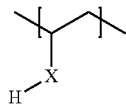 (V)

wherein X is as defined above.

Finally, the present invention provides the use of the a polymerizable polyacidic polymer, which is reactive with a reactive particulate glass in a cement reaction, in a cement reaction with a reactive particulate glass.

DETAILED DESCRIPTION OF THE PREFERRED EMBODIMENTS

According to the invention, a C1-6 alkyl group can include straight or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl. A cycloalkyl group may be a C3-6 cycloalkyl group. Examples of the cycloalkyl group can include those having 3 to 6 carbon atoms, for example, cyclopropyl, cyclobutyl, cyclopentyl and cyclohexyl. A cycloalkylalkyl group can include those having 4 to 8 carbon atoms. Examples for a cycloalkylalkyl group can include a combination of a straight or branched alkyl group having 1 to 6 carbon atoms and a cycloalkyl group having 3 to 6 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, and propylcyclopentyl.

The C1-6 alkyl group and the C3-8 cycloalkyl group may optionally be substituted by one or more members of the group selected from a C1-4 alkoxy group and a hydroxy group. Examples for a C1-4 alkyl group can include linear or branched alkyl groups having 1 to 4 carbon atoms, for example, methyl, ethyl, n-propyl, isopropyl, n-butyl, isobutyl, sec-butyl, tert-butyl. Examples for an C1-4 alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

The dental cement composition according to the present invention comprises a polymerizable polyacidic polymer having repeating units in the polymer backbone, which are represented by the following formula (I), (II), and/or (Ill):

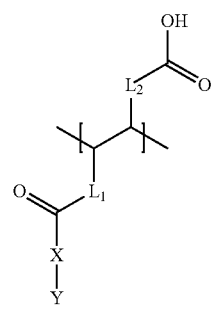 (I)

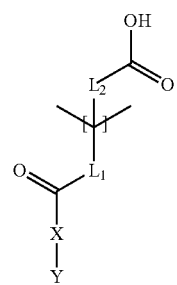 (II)

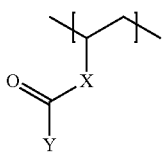

(III)

In a first specific embodiment, the polymerizable polyacidic polymer contains only repeating units in the polymer backbone, which are represented by only one of the above formula (I), (II), or (III).

In a second specific embodiment, the polymerizable polyacidic polymer contains repeating units in the polymer backbone, which are represented by two of the following formula (I), (II), or (III).

In a third specific embodiment, the polymerizable polyacidic polymer contains repeating units in the polymer backbone, which are represented by the above formula (I), (II), and (III).

In the above formula (I), (II), and (III), X represents O, S, or NR', whereby R' represents a hydrogen atom or a straight or branched C1-C6 alkyl group, C3-C6 cycloalkyl group, or C4-C8 cycloalkylalkyl group. Preferably, X represents O or NR', whereby R' represents a hydrogen atom or a straight or branched C1-C6 alkyl group.

In the above formula (I), (II), and (III), Y a group of the following formula (IV)

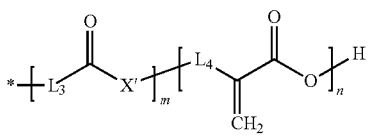

Each of L1, L2, L3 and L4 in any one of formula (I), (II), (III), and (IV), which are independent from each other, may represent a single bond, a straight or branched C1-C6 alkylene group, a straight or branched C1-C6 alkenylene, or a straight or branched C1-C20 alkylene group which includes 1 to 8 atoms selected from oxygen and sulfur atoms. A single bond, a straight or branched C1-C6 alkylene group or a straight or branched C1-C20 alkylene group which includes 1 to 8 atoms selected from oxygen and sulfur atoms are preferred.

In formula (IV), X' represents O, S, or NR", whereby R" represents a hydrogen atom or a straight or branched C1-C6 alkyl group, C3-C6 cycloalkyl group, or C4-C8 cycloalkylalkyl group. Preferably, X' represents O or NR", whereby R" represents a hydrogen atom or a straight or branched C1-C6 alkyl group.

In formula (IV), m is 0 to 3, preferably 0, 1 or 2,

In the above formula (IV), n is 1, 2 or 3.

The polymerizable polyacidic polymer having repeating units in the polymer backbone which are represented by the following formula (I) and/or (II) may be prepared by a process comprising the steps of
(i) copolymerizing a mixture containing acrylic acid and one or more monomers selected from the group of maleic anhydride and itaconic anhydride, and
(ii) reacting the reaction product of (i) with HXY, wherein X and Y are as defined above.

A polymerizable polyacidic polymer having repeating units in the polymer backbone which are represented by formula (III) may be prepared by a process comprising the steps of reacting a carboxylic acid anhydride of YCOOH, wherein Y is as defined above, with a polymer or copolymer containing repeating units of the following formula (V):

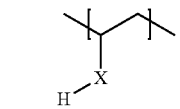

wherein X is as defined above.

A dental cement composition is preferably an aqueous dental glass ionomer composition comprising a reactive particulate glass and the polymerizable polyacidic polymer having specific repeating units in the polymer backbone as the reactive ionomer. The polymerizable polyacidic polymer according to the present invention may contain preferably carboxylic acid groups. However, a portion of the carboxylic acid groups may be present in the form of a salt. Suitable carboxylic acid salts are based on alkaline metal ions and ammonium ions.

A particulate reactive glass is a powdered metal oxide or hydroxide, mineral silicate, or ion leachable glass or ceramic, that is capable of reacting with an ionomer in the presence of water to form a hydrogel. The particulate glass may contain mixed oxides of Ca, Ba, Sr, Al, Si, Zn, Na, K, B, Ag, or P. Examples of particulate reactive glass materials include materials commonly known in the art of glass-ionomer cements such as calcium or strontium-containing and aluminum-containing materials. Preferably, particulate reactive fillers contain leachable fluoride ions.

Specific examples of particulate reactive glasses are selected from calcium aluminosilicate glass, calcium aluminumfluorosilicate glass, calcium aluminumfluoroborosilicate glass, strontium aluminosilicate glass, strontium aluminofluorosilicate glass, strontium aluminofluoroborosilicate glass.

Suitable particulate reactive glasses further include metal oxides such as zinc oxide and magnesium oxide, and ion-leachable glasses, e.g., as described in U.S. Pat. No. 3,655,605, U.S. Pat. No. 3,814,717, U.S. Pat. No. 4,143,018, U.S. Pat. No. 4,209,434, U.S. Pat. No. 4,360,605 and U.S. Pat. No. 4,376,835. In a preferred embodiment, the particulate glass is a barium and/or strontium fluoroalumosilicate glass.

According to a preferred embodiment, the reactive particulate glass contains silicon, aluminum, zinc, phosphorus and fluorine as essential elements, whereby silicon, aluminum, zinc and phosphorus are contained in the composition predominantly as oxides. Specifically, the reactive particulate glass may comprise
a. 10-35% by weight of silica
b. 10-35% by weight of alumina
c. 3-30% by weight of zinc oxide
d. 4-30% by weight of P2O5
e. 3-25% by weight of fluoride, Silica (calculated as SiO2) is preferably contained in the glass composition in an amount of from 10-35% by weight. In a more preferred embodiment, silica is contained in an amount of from 20-25% by weight. Alumina (calculated as Al2O3) is preferably contained in an amount of from 10-35% by weight. In a more preferred embodiment, alumina is contained in an amount of from 20-25% by weight. The weight ratio between silica and alumina is preferably in a range of from 1.2 to 0.8, more preferably in a range of from 1.15 to 1.0.

Zinc oxide (calculated as ZnO) is preferably contained in the glass composition used according to the invention in an amount of from 3-30% by weight. In a more preferred embodiment, zinc oxide is contained in an amount of from 13-18% by weight.

Phosphorus pentoxide (calculated as P2O5) is preferably contained in the glass composition used according to the invention in an amount of from 4-30% by weight. In a preferred embodiment, phosphorus pentoxide is contained in an amount of from 14 to 18% by weight.

Fluoride is preferably contained in the glass composition according to the invention in an amount of from 3-25% by weight. In a preferred embodiment, fluoride is contained in an amount of from 4-7% by weight.

Besides the preferred essential elements, the particulate glass composition of the present invention may further comprise from 18-21% by weight of calcium oxide plus strontium oxide.

The particulate glass composition preferably essentially does not contain any alkaline metal oxides. In particular, the glass composition contains at most 2% by weight, preferably at most 1.5% by weight, of alkaline metal oxides, M2O, wherein M is Li, Na, or K. In a preferred embodiment, the content of Na2O in the particulate glass is less than 1% by weight.

The particulate reactive glass may be surface modified by a surface modifying agent. The modifying compound is capable of reacting with surface atoms of the particulate reactive glass, thereby forming a covalent bond between the surface atoms of the particulate reactive glass and the modifying compound.

The surface modifying agent may contain a modifying compound providing a dual function. For example, the modifying compound may contain one or more functional groups capable of taking part in a crosslinking reaction, thereby facilitating the additional crosslinking, whereby the cured cement has improved flexural strength and fracture toughness. The modifying agent may contain one or more modifying compounds.

Preferably, the surface modifying agent contains a hydrolyzable organofunctional silicon compound. The hydrolyzable organofunctional silicon compound may be a compound of one of the following formulae (II), (III) and (IV), or a hydrolysis product thereof X'$_m$R$_{3-m}$SiL (II')

X'$_m$R$_{2-m}$SIL'L" (III')

X'$_m$SiL'L"L'" (IV')

wherein
X'
represents a hydrolyzable group;
R
represents an alkyl, cycloalkyl, cycloalkylalkyl, aralkyl or aryl group,
L, L', L", and L'"
which may be the same or different represent independent from each other an organic group containing one or more —S$_x$H groups, wherein x is an integer of from 1 to 6;
m
is an integer of at least 1,
whereby the sum of X, R, L, L', L", and L'" is 4 for each of formula (II'), (III'), and (IV').

Preferably, X is a halogen atom or OR1, wherein R1 is an alkyl, cycloalky, cycloalkylalkyl, aralkyl or aryl group. More preferably, R or R1 are independently an alkyl group.

In order to impart crosslinking capability to the organofunctional silicon compound, L, L', L", and L'" may contain —S$_x$H groups, wherein x is an integer of from 1 to 6, preferably 1, or a polymerizable group, such as a (meth) acrylate group, a (meth)acrylamide group, an allyl group or a vinyl group.

In a preferred embodiment, L, L', L", and L'" may be represented by the following formula:

[(CH2)OZ']$q$(CH2)$p$Liv wherein
the Z' which may be the same or different and are independent from each other, represent —NR'—, —O—, S or PR', wherein R' represents independently a hydrogen atom, an alkyl group, a cycloalkyl group, an cycloalkylalkyl group, an aralkyl group or an aryl group,
Liv represents a linear or branched polymer moiety comprising specific repeating units (I), (II) and/or (III) as defined above in the polymer backbone, or SxH, or a polymerizable double bond such as a (meth)acrylate group, a (meth) acrylamide group, an allyl group or a vinyl group, or
a group a group of the following formula (IV)

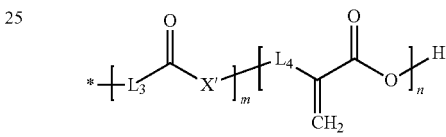

wherein each L3 and L4 which are independent from each other represents a single bond or a straight or branched C1-C6 alkylene group or a straight or branched C1-C6 alkenylene group, X' represents O, S, or NR", whereby R" represents a hydrogen atom or a straight or branched C1-C6 alkyl group, C3-C6 cycloalkyl group, or C4-C8 cycloalkylalkyl group,
and p, which are independent from each other, may be the same or different and represent an integer
of from 1 to 6,
q represents an integer of from 0 to 12, and
x is an integer of from 1 to 6.

In a further preferred embodiment, L, L', L", and L'" may be represented by the following formula:

—[(CH2)$o$NR']$q$(CH2)$p$Liv wherein
R', which are independent from each other, may be the same or different and represent a hydrogen atom, an alkyl group, a cycloalkyl group, an cycloalkylalkyl group, an aralkyl group or an aryl group, Liv represents a linear or branched polymer moiety comprising acidic groups and having a polymer backbone containing specific repeating units (I), (II) and/or (III) as defined above, or SxH, or a polymerizable double bond such as a (meth)acrylate group, a (meth) acrylamide group, an allyl group or a vinyl group, or a group of the following formula (IV)

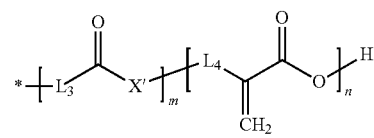

wherein each L3, L4, and X' are as defined above, and p, which are independent from each other, may be the same or different and represent an integer of from 1 to 6, q represents an integer of from 0 to 12 and
x is an integer of from 1 to 6.

In a still further preferred embodiment, L, L', L", and L'" may be represented by the following formula:

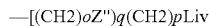

wherein
Z" represents an oxygen atom or a sulfur atom;
Liv represents a linear or branched polymer moiety comprising acidic groups and having a polymer backbone comprising specific repeating units (I), (II) and/or (III) as defined above, o and p, which are independent from each other, may be the same or different and represent an integer of from 1 to 6, and q represents an integer of from 0 to 12.

Specific examples of modifying compounds contained in the surface modifying agent used in the present invention are 3-mercaptopropyltrimethoxysilane, 3-mercaptopropylmethyldimethoxysilane, 3-mercaptopropyldimethylmethoxysilane, 3-mercaptopropyltriethoxysilane, 3-mercaptopropylmethyldiethoxysilane,
3-mercaptopropyldimethylethoxysilane. The compounds may be used alone or in combination of two or more different compounds.

Based on the treatment of the particulate reactive glass with the surface active agent, the surface of the reactive filler may display functional groups such as Liv groups or groups of the formula (IV) which may be used for additional curing reactions such as Michael additions of SxH groups to alpha, beta unsaturated ester groups, oxidative coupling reactions of SxH groups, en-type reactions, condensation reactions or radical polymerizations.

The surface modifying agent may be used as such or dissolved or dispersed in a suitable solvent. Examples of suitable solvent are toluene, methanol, ethanol, isopropanol, and ethylacetate.

The particulate reactive glass usually has an average particle size of from 0.005 to 100 μm, preferably of from 0.01 to 40 μm as measured using, for example, by electron microscopy or by using a conventional laser diffraction particle sizing method as embodied by a MALVERN Mastersizer S or MALVERN Mastersizer 2000 apparatus. The particulate reactive glass may be a multimodal particulate reactive glass representing a mixture of two or more particulate fractions having different average particle sizes. The particulate reactive glass may also be a mixture of particles of different chemical composition. In particular, it is possible to use a mixture of a particulate reactive material and a particulate non-reactive material.

The aqueous dental glass ionomer composition according to the invention preferably comprises 20 to 80 percent by weight, more preferably 40 to 70 percent by weight, of the reactive particulate glass, based on the weight of the entire composition.

Furthermore, the dental cement composition of the present invention may optionally further comprise dispersed nanoparticles comprising grafted linear or branched polymer chains comprising acidic groups, and having a polymer backbone. The polymer backbone may also comprise repeating units in the polymer backbone, which are represented by the formula (I), (II), and/or (III) as defined above, which is reactive with the particulate glass in a cement reaction.

The aqueous dental glass ionomer composition according to the invention further comprises a polymerizable polyacidic polymer having repeating units in the polymer backbone, which are represented by the formula (I), (II), and/or (III) as defined above, which is reactive with the particulate glass in a cement reaction.

In a first preferred embodiment, the polymerizable polyacidic polymer contains repeating units in the polymer backbone, which are represented by the formula (I).

In a second preferred embodiment, the polymerizable polyacidic polymer contains repeating units in the polymer backbone, which are represented by the formula (II).

In a third preferred embodiment, the polymerizable polyacidic polymer contains repeating units in the polymer backbone, which are represented by the formula (I) and (II).

In a fourth preferred embodiment, the polymerizable polyacidic polymer contains repeating units in the polymer backbone, which are represented by the formula (III).

The polymerizable polyacidic polymer may be a linear or branched polymer and may comprises acidic groups. The a polymerizable polyacidic polymer has a polymer backbone and optionally additional pendant groups. The backbone may comprise acidic groups and optionally the pendant groups may comprise acidic groups. The acidic groups are preferably carboxylic acid groups.

The polymerizable polyacidic polymer having repeating units in the polymer backbone which are represented by the formula (I) and/or (II) as defined above may be prepared by a process comprising the steps of
(i) copolymerizing a mixture containing acrylic acid and one or more monomers selected from the group of maleic anhydride, itaconic anhydride, and
(ii) reacting the reaction product of (i) with HXY, wherein X and Y are as defined above.

The copolymerization conditions are not particularly limited. Preferably, in step (i) a mixture containing polymerizable monomers is dissolved in a suitable solvent such as distilled water or an aqueous mixture containing a water miscible alcohol such as ethanol, and after flushing with nitrogen, an initiaor molecule such as 2,2'-azobis[2-(2-imidazolin-2-yl)propane]dihydrochloride is added. The mixture may contain further monomers as the case requires. Preferred comonomers are acrylic acid, methacrylic acid, itaconic acid, itaconic acid anhydride, maleic acid, maleic anhydride, fumaric acid, methyl acrylate, ethyl acrylate, n-butyl acrylate, t-butyl acrylate, 2-ethylhexyl acrylate, methyl methacrylate, ethyl methacrylate, n-butyl methacrylate, t-butyl methacrylate, 2-ethylhexyl methacrylate, cyclohexyl methacrylate, phenyl acrylate, benzyl acrylate, phenyl methacrylate, benzyl methacrylate, 2-phenylethyl methacrylate, 2-hydroxyethyl acrylate, 2-hydroxyethyl methacrylate, hydroxypropyl acrylate, styrene, 8-methylstyrene, vinylpyridine, N-vinylpyrrolidone, vinyl carbazole, vinyldene halide, acrylonitrile, t-butyl acrylate, ethyl methacrylate, n-butyl methacrylate, ethyl triethyleneglycol methacrylate, n-dodecyl acrylate, n-dodecyl methacrylate, 1-tetradecyl methacrylate, 1-hexadecyl acrylate, 1-hexadecyl methacrylate, n-octadecyl acrylate, n-octadecyl methacrylate, tetrahydrofurfuryl acrylate, tetrahydrofurfuryl methacrylate, tetrahydropyranyl methacrylate, phenyl acrylate, benzyl acrylate, 2-cyanoethyl acrylate, 2-hydroxyethyl acrylate, hydroxypropyl acrylate, hydroxypropyl methacrylate, 2,3-dihydroxypropyl acrylate, 2,3-dihydroxypropyl methacrylate, poly(ethylene glycol)(n)monomethacrylate with n=200 and 400, poly(ethylene glycol)(n)monomethyl ether monomethacrylate with n=200; 400 and 1000, 2-isocyanatoethyl acrylate, 2-isocyanatoethyl methacrylate, glycidyl acrylate, glycidyl methacrylate, 2-sulfoethyl methacrylate, 3-sulfopropyl acrylate, 2,2,2-trifluoroethyl acrylate, 2,2,2-trifluoroethyl methacrylate, styrene, a-methylstyrene, 4-cyanostyrene, 4-chlorostyrene, chloromethylstyrene, vinylpyridine, vinyl carbazole, vinylidene halides, acrylonitrile, methacrylonitrile, acrylamide, methacrylamide, N-benzylacrylamide, N-hydroxymethylacrylamide, hydroxymethyldiacetoneacrylamide, N-(2-hydroxypropyl)methacrylamide, vinyl acetate, and N-vinylpyrrolidone.

The polymerizable compounds may preferably be selected from the group of acrylic acid, methacrylic acid, itaconic acid, itaconic acid anhydride, maleic acid, maleic anhydride, fumaric acid, methyl acrylate, ethyl acrylate, n-butyl acrylate, t-butyl acrylate, 2-ethylhexyl acrylate, methyl methacrylate, ethyl methacrylate, n-butyl methacrylate, t-butyl methacrylate, 2-ethylhexyl methacrylate, cyclohexyl methacrylate, phenyl acrylate, benzyl acrylate, phenyl methacrylate, benzyl methacrylate, 2-phenylethyl methacrylate, 2-hydroxyethyl acrylate, 2-hydroxyethyl methacrylate, hydroxypropyl acrylate, styrene, 8-methylstyrene, vinylpyridine, N-vinyl pyrrolidone, vinyl carbazole, vinyldene halide, and acrylonitrile.

The reaction time may be from 5 minutes to 120 hours, preferably from 2 to 48 hours in order to complete the reaction. The reaction temperature may be between room temperature and the boiling temperature of the solvent. After reaction is terminated, the reaction product may be isolated by precipitation in acetone. The copolymer may be purified by dissolving in water and lyophilization.

Subsequently, the copolymer is reacted with HXY, wherein X and Y are as defined above. Accordingly, the copolymer may be added to a solution of HXY in a suitable solvent such as dichloromethane in the presence of a suitable catalyst such as N-ethyl-diisopropylamine and an inhibitor such as 2,6-di-tert-butyl-4-methyl-phenol (BHT). The reaction is preferably accelerated by irradiation of microwave energy, preferably with an energy of 0.5 to 100 Watts, more preferably 1 to 10 Watts. The reaction time may be from 1 minute to 12 hours, preferably from 2 minutes to 30 minutes in order to complete the reaction. The reaction temperature may be between room temperature and the boiling temperature of the solvent. Preferably, the irradiation of microwave energy is according to the following formula at room temperature and atmospheric pressure 5 W·min ≤ s (irradiation energy W)(irradiation time min) ≤ 100 W·min Preferably, the irradiation of microwave energy is ≤80 W·min. The synthesis may be carried out according to Goretzki Ch. et al. Macromol. Rapid Commun. 2004, 25, 513-516.

The product may be isolated by dissolution in water, and purified by reprecipitation in acetone. Purification may be carried out by lyophilization.

The polymerizable polyacidic polymer having repeating units in the polymer backbone which are represented by the formula (III) may be prepared by a process comprising the steps of reacting a carboxylic acid anhydride of YCOOH, wherein Y is as defined above, with a polymer or copolymer containing repeating units of the following formula (V):

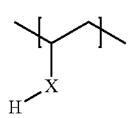
(V)

wherein X is as defined above.

In any one of formulae (I), (II), and (III), X represents O, S, or NR', whereby R' represents a hydrogen atom or a straight or branched C1-C6 alkyl group, C3-C6 cycloalkyl group, or C4-C8 cycloalkylalkyl group. According to a preferred embodiment, X represents O or NH in order to provide a polymerizable polyacidic polymer having good water solubility.

It is possible to create a source of additional covalent cross-linking, which imparts additional strength to the ultimate ionomeric cement composition, by reacting a portion of the carboxylic acid groups or carboxylic acid anhydride groups with a further bifunctional monomer containing a carbon-carbon double bond which can take part in an ene-type reaction with —SxH groups present in the composition, and/or with a bifunctional monomer containing a reactive alpha,beta-unsaturated moiety which can take part in Michael addition reaction with the —SxH groups present in the composition, and optionally in a radical polymerization reaction.

In any one of formulae (I), (II), and (III), X represents O, S, or NR', whereby R' represents a hydrogen atom or a straight or branched C1-C6 alkyl group, C3-C6 cycloalkyl group, or C4-C8 cycloalkylalkyl group.

Preferably X represents O, or NR', whereby R' represents a hydrogen atom or a straight or branched C1-C6 alkyl group.

In any one of formulae (I), (II), and (III), Y represents a group of the formula (IV) wherein each of L1, L2, L3 and L4, which are independent from each other represents a single bond or a straight or branched C1-C6 alkylene group or a straight or branched C1-C6 alkenylene, X' represents O, S, or NR", whereby R" represents a hydrogen atom or a straight or branched C1-C6 alkyl group, C3-C6 cycloalkyl group, or C4-C8 cycloalkylalkyl group.

Preferably, Y represents a group of the formula (IV) wherein each of L1, L2, L3 and L4, which are independent from each other represents a single bond or a straight or branched C1-C6 alkylene group, X' represents O or NR", whereby R" represents a hydrogen atom or a straight or branched C1-C6 alkyl group.

By incorporating the specific polymer backbone according to the invention into the ionomer cement, not only the brittleness may be further improved, but also the mechanical strengths and physical properties are improved, while at the same time the water solubility of the polymerizable polyacidic polymer is not deteriorated as compared to a corresponding polyacid polymer which does not contain the polymerizable moieties linked to an acidic group.

The linear or branched polymer comprising acidic groups preferably has a molecular weight Mw in the range of from 1,000 to 1000,000, more preferably 5,000 to 400,000.

The aqueous dental glass ionomer composition according to the invention preferably comprises 10 to 80 percent by weight, more preferably 15 to 55 percent by weight, of the linear or branched polymer containing acidic groups, based on the weight of the entire composition.

The aqueous dental glass ionomer composition according to the invention may comprise from 0 to 75 percent by weight of dispersed nanoparticles based on the weight of the entire composition. Preferably, the composition contains 5 to 50 percent by weight of dispersed nanoparticles based on the weight of the entire composition. In a preferred embodiment, the dispersed nanoparticles have an average particle size of from 1 to 100 nm.

The glass ionomer composition of the present invention may optionally further contain a low molecular compound. The low molecular compound may have a molecular weight Mw in the range of from 100 to 5000, preferably in the range of from 200 to 2000. The low molecular compound may contain one or more —SxH groups, wherein x is an integer of from 1 to 6. Alternatively, the low molecular compound may contain moieties which may react with the —SxH groups present in the glass ionomer composition in an ene-type reaction or a Michael addition reaction. Specific examples for suitable polythiol compounds are PEG dithiol (e.g. Aldrich 704369, average molecular weight: 1,500; Aldrich704539 average molecular weight: 3,400), 1,16-Hexadecanedithiol, peptides such as Asn-Arg-Cys-Ser-Gln-Gly-Ser-Cys-Trp-Asn, Reduced=85% (HPLC) C44H67N1701652, 1154.24. Trithiocyanuric acid, tetrathiol- and tetrapyrrole-substituted Tetrathiafulvalene derivatives, pentaerythrityl tetrathiol, trimethylolpropane tris(2-mercaptoacetate), trimethylolpropane tris(3-mercaptopropionate), 2,2'-(ethylenedioxy) diethanethiol and pentaerythritol tetrakis(3-mercaptopropionate).

The glass ionomer composition of the present invention may comprise —SxH groups, wherein x is an integer of from 1 to 6, which crosslink the particulate glass and/or the linear polymer comprising acidic groups and/or the optionally dispersed nanoparticles and/or the low molecular compound. The —SxH groups, wherein x is an integer of from 1 to 6, are sulfane or polysulfane groups, wherein x is preferably 1 to 3. Specifically, the —SxH groups are preferably thiol groups (—SH), disulfane groups (—S—SH) or trisulfane groups (—S—S—SH). In a more preferred embodiment —SxH groups are thiol groups which may be primary or secondary thiol groups.

When the crosslinking reaction is based on an oxidative coupling of —SxH groups, the —SxH groups, wherein x is an integer of from 1 to 6, may be present on any of the reactive particulate glass, the linear or branched polymer containing acidic groups, the optional dispersed nanoparticles, or on the optional low molecular compound present in the composition. Preferably, oxidative coupling is metal catalyzed oxidative coupling in the presence of an oxidizing agent. Accordingly, the composition contains preferably a transition metal ions and an oxidizing agent. Examples of the transition metal ions are iron and manganese ions. Moreover, the composition preferably contains an oxidizing agent. Examples for a suitable oxidizing reagent are peroxides such as hydrogen peroxide or a peroxide compound commonly used as free-radical polymerization initiators.

In a first preferred embodiment, the —SxH groups are present exclusively on either the reactive particulate glass, the linear or branched polymer containing acidic groups, or the optional dispersed nanoparticles. In case the —SxH groups are present exclusively on an optional additional low molecular component present in the composition, then it will be necessary that the reactive particulate glass, the linear or branched polymer containing acidic groups, and/or the optional dispersed nanoparticles contain reactive carbon-carbon double bonds which may take part in an ene-type reaction or a Michael addition with the —SxH groups. Specifically, the —SxH groups may be present on the linear or branched polymer containing acidic groups.

In a second preferred embodiment, the —SxH groups are present on at least two members selected from the group of either the reactive particulate glass, the linear or branched polymer containing acidic groups, the optional dispersed nanoparticles, or the optional low molecular compound. Any other member selected from this group may contain reactive carbon-carbon double bonds which may take part in an ene-type reaction or the Michael addition with the —SxH groups.

In a third preferred embodiment each of the members selected from the group of the reactive particulate glass, the linear or branched polymer containing acidic groups, the optional dispersed nanoparticles, or the optional low molecular compound contains either —SxH groups or reactive carbon-carbon double bonds which may take part in an ene-type reaction with the —SxH groups.

Accordingly, in the aqueous dental glass ionomer composition according to the invention, the —SxH groups may crosslink the particulate glass and/or the linear or branched polymer containing acidic groups and/or the optionally dispersed nanoparticles by oxidative coupling.

In a further preferred embodiment, the sulfane or polysulfane groups of the aqueous dental glass ionomer composition according to the invention crosslink the particulate glass and/or the linear polymer containing acidic groups and/or the optionally dispersed nanoparticles in the absence of oxygen. Preferably, the —SxH groups in the aqueous dental glass ionomer composition according to the invention crosslink by an —SxH ene-reaction or a Michael addition.

The dental glass ionomer compositions of the present invention may further contain catalysts for the cross-linking reaction, a retarder, free-radical polymerization initiators, stabilizers, non-reactive fillers, solvents, pigments, nonvitreous fillers, free radical scavengers, polymerization inhibitors, reactive and nonreactive diluents, coupling agents to enhance reactivity of fillers, rheology modifiers, and surfactants (such as to enhance solubility of an inhibitor e. g., polyoxyethylene).

Suitable catalysts for the cross-linking reaction may comprise metal cations, metal complexes and/or metal particles such as metal powder or metal colloids, either alone or in combination with an oxidizing agent such as oxygen, a peroxide and/or an oxidizing metal complex, In one aspect, the catalyst and oxidizing agent may comprise the same material. The metal cations, metal complexes and/or metal particles may comprise iron, nickel, copper, cobalt or platinum atoms, or the corresponding ions thereof. The peroxide may comprise hydrogen peroxide, urea-hydrogen peroxide, ethylmethylketone peroxide, or benzoylperoxide.

Suitable retarders are low molecular weight compounds having multiple carboxylic acid groups such as tartraic acid.

Suitable radical polymerization initiators may be selected from the following classes of initiator systems:

Combinations of an organic peroxide and an amine, wherein the organic peroxide may be benzoyl peroxide or a thermally more stable peroxide such as 2,5-dimethyl-2,5-di(benzolyperoxy)hexane, tert.-butylamyl peroxide, di-(tert.-butyl) peroxide, cumene hydroperoxide, tert.-butylhydroperoxide, tert.butyl-peroxy-(3,5,5-trimethyl hexanoate), tert.-butylperoxy benzoate and tert.butylperoxy-2-ethylhexyl carbonate. The amine compound may be an aromatic amine compound such as DMABE.

Combinations of an organic peroxide, a reducing agent and a suitable metal ion. The peroxide may be selected from benzoyl peroxide, 2,5-dimethyl-2,5-di(benzolyperoxy) hexane, tert.-butylamyl peroxide, di-(tert.-butyl) peroxide, cumene hydroperoxide, tert.-butylhydroperoxide, tert.butyl-peroxy-(3,5,5-trimethyl hexanoate), tert.-butylperoxy benzoate and tert.butylperoxy-2-ethylhexyl carbonate. The reducing agent may be a protected reducing agent in inactive form, which forms an active reducing agent as disclosed in EP 0 951 894. The metal ion may be a salt of a metal or an organometalic compound, which may be present as an acetate, salicylate, naphenoate, thiourea complex, acetylacetonate or ethylene tetramine acidic acid. Suitable metal ions are selected from copper, iron, and silver.

Combinations of a hydroperoxide and a metal ion. A suitable hydroperoxide is hydrogen peroxide. A suitable metal may be selected from iron and copper.

Transition metal carbonyl compounds such as dicopper octacarbonyl complexes which may from radical species.

Alkylboron compounds such as alkyl boranes.

Combinations of peroxdisulphate salts and thiol compounds.

Provided that the dental restorative composition is applied as a thin layer, or in case the refractive index of the polymerizable matrix and the filler are similar, it is possible to use a photopolymerization initiator. Suitable photopolymerization initiators may include camphor quinone in combination with an amine.

Suitable stabilizers may be selected from reducing agents such as vitamin C, inorganic sulfides and polysulfides and the like.

Suitable non-reactive fillers may be selected from fillers currently used in dental restorative compositions. The filler should be finely divided and preferably has a maximum particle diameter less than about 100 μm and an average particle diameter less than about 10 μm. The filler may have a unimodal or polymodal (e.g., bimodal) particle size distribution. The filler can be an inorganic material. It can also be a crosslinked organic material that is insoluble in the polymerizable resin, and is optionally filled with inorganic filler. The filler can be radiopaque, radiolucent or non-radiopaque.

Examples of suitable non-reactive inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas.

Examples of suitable non-reactive organic filler particles include filled or unfilled pulverized polycarbonates or polyepoxides.

Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

Suitable solvents or nonreactive diluents include alcohols such as ethanol and propanol. Suitable reactive diluents are alpha,beta unsaturated monomers for providing altered properties such as toughness, adhesion, and set time, e.g., 2-hydroxyethyl methacrylate (HEMA), hydroxypropyl methacrylate.

Suitable alpha,beta-unsaturated monomers may be water-soluble, water-miscible or water-dispersible. Water-soluble, water-miscible or water-dispersible acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Moreover, a further preferred group of compounds are diallyl compounds such as diallyl amine.

Mixtures of alpha,beta-unsaturated monomers can be added, if desired. Preferably, the mixed but unset cements of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset cement components.

An example of a suitable free radical scavenger is 4-methoxyphenol.

Suitable polymerization inhibitors may be selected from hydroxytoluene, butylated hydroxytoluene (BHT), hydroquinone, 1,4-benzoquinone, tert-butylpyrocatechol, toluhydroquinone, and 3,4-di-tert-butyl-p-cresol. The amount of inhibitor may be selected from 0.001 to 2% and preferably from 0.02 to 0.5% based on the total weight of the copolymer/comonomer/water mixture.

External energy may alternatively or additionally be employed in order to crosslink the —SxH groups by oxidative coupling. Sources of external energy may be selected from radiative energy sources such as thermal energy sources, ultrasound energy sources, and/or light energy sources such as ultraviolet lamps or visible lamps. In the event that light energy is employed to crosslink the —SxH groups by oxidative coupling, the dental glass ionomer composition may additionally comprise photoinitiators and/or photosensitizers such as molecular oxygen, alpha-diketones, orthoquinones, organic dyes, fluorescent dyes or colorants, and/or azo-compounds such as azobisisobutyronitrile and 1,1'azobis(cyclohexanecarbonitrile).

The dental glass ionomer composition may be used in a dental ionomer cement. Two major classes of such cements may be distinguished. The first class relates to conventional glass ionomers employing as their main ingredients a homopolymer or copolymer of an alpha,beta-unsaturated carboxylic acid (e.g., poly acrylic acid, copoly (acrylic, itaconic acid), etc.), a modified particulate reactive filler such as modified fluoroaluminosilicate glass, water, and a chelating agent such as tartaric acid. Such dental ionomer cements may be supplied in powder/liquid formulations that are mixed just before use. The mixture will undergo self-hardening in the dark due to an ionic reaction between the acidic groups of the polycarboxylic acid and cations leached from the glass as well as the crosslinking reaction based on the —SxH groups. The second major class relates to resin-modified glass ionomer cements. Like a conventional glass ionomer, a resin-modified glass ionomer cement employs a modified particulate reactive filler obtainable according to the process of the present invention, whereby the organic portion of an resin-modified glass ionomer cements is different. In one type of resin-modified glass ionomer cement, the polycarboxylic acid is modified to replace or end-cap some of acidic repeating units with pendent curable groups and a photoinitiator is added to provide a second cure mechanism, e.g., as in U.S. Pat. No. 5,130,347. Acrylate or methacrylate groups may be employed as the pendant curable group. A redox cure system can be added to provide a third cure mechanism, e.g., as in U.S. Pat. No. 5,154,762. In another type of resin-modified glass ionomer cement, the cement includes a polycarboxylic acid, an acrylate or methacrylate-functional monomer and a photoinitiator, e.g., as in Mathis et) and as in U.S. Pat. No. 5,063,257, U.S. Pat. No. 5,520,725, U.S. Pat. No. 5,859,089 and U.S. Pat. No. 5,962,550. Various monomer-containing or resin-containing cements are also shown in U.S. Pat. No. 4,872,936, U.S. Pat. No. 5,227,413, U.S. Pat. No. 5,367,002 and U.S. Pat. No. 5,965,632. Resin-modified glass ionomer cements may be formulated as powder/liquid or paste/paste systems, and contain water as mixed and applied. They harden in the dark due to the ionic reaction between the acidic groups of the polycarboxylic acid and cations leached from the glass as well as the crosslinking reaction of the particulate glass and/or the linear polycarboxylic acid and/or the optionally dispersed nanoparticles when the pH of the aqueous dental glass ionomer composition is at least 6 at the end of the main setting reaction of the linear polycarboxylic acid reactive with the particulate glass. Moreover, resin-modified glass ionomer cements also cure on exposure of the cement to light from a dental curing lamp.

Methods for preparing the glass ionomer compositions are well known. (Crisp et al., "Glass ionomer cement formulations. II. The synthesis of novel polycarboxylic acids," in J. Dent. Res. 59 (6): 1055-1063 (1980)). A dental ionomer cement is prepared by mixing the ionomer with the particulate reactive filler and optionally nanoparticles in the presence of water. The components of the ionomer cement system can be combined (such as by mixing or blending) in a variety of manners and amounts in order to form the ionomer cements of the present invention. For example, a concentrated aqueous solution of the ionomer may be mixed with the modified particulate reactive filler and optionally further components at the time of use. The resultant combination of ionomer, modified particulate reactive filler and water allows the setting reaction to begin. Alternatively, the ionomer and the modified particulate reactive filler are provided as a freeze-dried or lyophilized powdered blend under conditions in which there is not sufficient water to allow the setting reaction to proceed. Such systems can then be combined with water at the time of use in order to begin the setting reaction. Once the setting reaction has begun, the resultant mixture may be formed into its desired shape, followed by curing and allowing the mixture to fully harden. In general, the weight-to-weight ratio of the ionomer to water is from about 1:10 to about 10:1. In general, the concentration of ionomer in water ranges from 25 to 90% by weight, and preferably from 40 to 65% by weight. The resultant aqueous solution has a ratio of polymer to liquid generally ranging from about 1.5 to 8.

The reaction mixture may also include a retarding or modifying agent such as tartaric acid, for adjusting the working time and a setting time, respectively, when preparing the cement as described in U.S. Pat. No. 4,089,830, U.S. Pat. No. 4,209,434, U.S. Pat. No. 4,317,681 and U.S. Pat. No. 4,374,936. In general, an increase in working time results in an increase in setting time as well. The "working time" is the time between the beginning of the setting reaction when the ionomer and modified particulate reactive filler are combined in the presence of water, and the time the setting reaction proceeds to the point when it is no longer practical to perform further physical work upon the system, e.g. spatulate it or reshape it, for its intended dental or medical application. The "setting time" is the time measured from the beginning of the setting reaction in a restoration to the time sufficient hardening has occurred to allow subsequent clinical or surgical procedures to be performed on the surface of the restoration.

In the setting reaction, the modified particulate reactive glass behaves like a base and reacts with the acidic ionomer to form a metal polysalt which acts as the binding matrix (Prosser, J. Chem. Tech. Biotechnol. 29: 69-87(1979)). Moreover, due to the presence of —SxH groups, crosslinking of the particulate glass and/or the linear polycarboxylic acid and/or the optionally dispersed nanoparticles when the pH of the aqueous dental glass ionomer composition is at least 6 during the reaction of the linear polycarboxylic acid reactive with the particulate glass takes place. Thereby the bonding within the cement does not only rely on ionic salt bridges which are problematic with regard to the mechanical properties, but also on covalent and complex bonding. The setting reaction is therefore characterized as a dual chemical cure system that proceeds automatically in the presence of water. The cement sets to a gel-like state within a few minutes and rapidly hardens to develop strength. Further reactions are polymerisation reactions and polyaddition reactions.

The dental composition is a multi-pack, preferably a two-pack composition. The composition may be a paste/paste system, a powder/liquid system, or a liquid/paste system. The composition is designed so as to avoid premature curing of the components. For this purpose, the reactive inorganic filler component and any acid group containing component must be formulated so as to avoid a premature cement reaction. In a first embodiment, the reactive inorganic glass is contained in a first pack and any acid group containing component is contained in a second pack. The first pack may be a powder or a paste. The second pack may be a liquid or paste. In a second embodiment, the first pack is a powder comprising the reactive inorganic filler and a solid polyacidic polymer such as polyacrylic acid, and the second pack is a paste or liquid and contains a further acid group containing component.

The ratio of powder to liquid affects the workability of the mixed ionomer cement systems. Weight ratios higher than 20:1 tend to exhibit poor workability, while ratios below 1:1 tend to exhibit poor mechanical properties, e. g., strength, and hence are not preferred. Preferred ratios are on the order of about 1:3 to about 6:1 and preferably about 1:1 to 4:1.

The invention will now be further illustrated by the following Examples. All percentages refer to percentages by weight unless stated otherwise.

EXAMPLES

Example 1 Synthesis of Hydroxymethylacrylate According to J. W. Stansbury, Macromolecules, 1993, 26, 2981-2982

10.0 g (100.0 mmol) acrylic acid ethylester, 2.2 g (72.0 mmol) paraformaldehyde and 0.8 g (7.2 mmol) 1,4-diazabicyclo[2.2.2]octane (DABCO) were mixed and stirred at room temperature until the solution became clear. 3.0 g (23%) of hydroxymethyl acrylate were isolated by column chromatography using ethyl acetate and n-hexane (1:1) as eluents.

1H-NMR [ppm]: δ (500 MHz, CDCl3)=1.3 (CH3-CH2); 3.2 (HO—CH2); 4.2 (HO—CH2); 4.3 (CH3-CH2-0); 5.85 (=CH2); 6.25 (=CH2)

Example 2 Synthesis of Hydroxymethylacrylic Acid 1.0 g (7.7 mmol) hydroxymethyl acrylate was dissolved in 1.5 mol 5 weight-% sodium hydroxide solution (0.46 g; 11.6 mmol NaOH) and stirred for 4 hours at room temperature. After several extractions with diethyl ether, the ether phase was washed with water, dried over calcium chloride and the product was dried in vacuum. Yield: 0.47 g (60%)

1H-NMR [ppm]: δ (500 MHz, CDCl3)=3.2 (HO—CH2); 4.2 (HO—CH2); 5.85 (=CH2); 6.25 (=CH2); 12.5 (O=C—OH)

Example 3 Copolymerisation of Acrylic Acid (AA) and Itaconic Anhydride (IA)

1.0 g (13.9 mmol) acrylic acid and 1.56 g (13.9 mmol) itaconic anhydride were dissolved in distilled water. After flushing with nitrogen for 30 minutes 0.4494 g (0.139 mmol) 2,2'-azobis[2-(2-imidazolin-2-yl)propane]dihydrochloride as initiator were added. It was stirred at 60° C. for 24 hours under nitrogen. The polymer was reprecipitated in acetone, dissolved in water and lyophilized. To remove all residues the polymer powder was stirred in chloroform for one hour, filtrated and dried under vacuum. Yield: 2.23 g 13C-NMR [ppm]: δ (500 MHz, D2O)=33.4-47.5 (CH/CH2); 174.4 (C=O anhydride); 177-180 (C=O acid)

Example 4 Ring-Opening of Itaconic Anhydride in the Copolymer of Acrylic Acid and Itaconic Anhydride 0.20 g (1.62 mmol) 4-Dimethylamino pyridine, 1.40 g (10.86 mmol) N-ethyl-diisopropyl amine, 0.55 g (5.4 mmol) hydroxymethylacrylic acid and 0.04 g (0.18 mmol) 2,6-di-tert-butyl-4-methyl-phenol (BHT) were dissolved in 2.80 g dichlormethane. 1.00 g copolymer of acrylic acid and itaconic anhydride was added and the dichlormethane was removed under vacuum. The reaction mixture was put into a vial and closed for microwave reaction. It was irradiated for 10 minutes with 5 W. Afterwards, the product was dissolved in water, reprecipitated in acetone, and then dissolved in water for lyophilization. The polymer powder was stirred in isopropanol for one hour and was dried under vacuum. Yield: 0.83 g 13C-NMR [ppm]: δ (500 MHz, D2O)=33.4-47.5 (CH/CH2backbone); 174.4 (C=O anhydride); 177-180 (C=O acid); monomer: 62 (O—CH2-C=); 127 (CH2=C); 142 (C=CH2); 173 (C=O)

What is claimed:
1. Dental cement composition comprising a polymerizable polyacidic polymer having repeating units in the polymer backbone, which are represented by the following formula (I), (II), and/or (III):

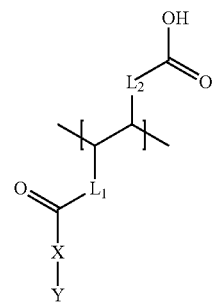

(I)

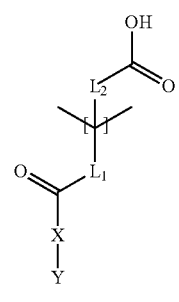

(II)

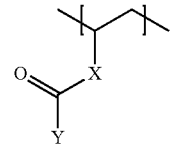

(III)

wherein
X represents O, S, or NR', whereby R' represents a hydrogen atom or a straight or branched $C_1$-$C_6$ alkyl group, $C_3$-$C_6$ cycloalkyl group, or $C_4$-$C_8$ cycloalkylalkyl group,
Y represents a group of the following formula (IV)

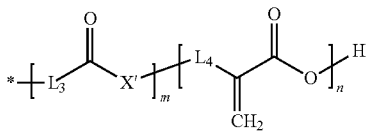

wherein each of $L_1$, $L_2$, $L_3$ and $L_4$,
which are independent from each other represents a single bond, a straight or
branched $C_1$-$C_6$ alkylene group, a straight or branched C alkenylene, or a straight or branched $C_1$-$C_{20}$ alkylene group which includes 1 to 8 atoms selected from oxygen and sulfur atoms,
X' represents O, S, or NR", whereby R" represents a hydrogen atom or a straight or branched $C_1$-$C_6$ alkyl group, $C_3$-$C_6$ cycloalkyl group, or $C_4$-$C_8$ cycloalkylalkyl group,
m is 0 to 3, and
n is 1 to 3, and
wherein the dental cement composition further is a particulate glass comprising
(a) 20-25% by weight of silica
(b) 20-25% by weight of alumina
(c) 18-21% by weight of CaO plus SrO
(d) 13-18% by weight of zinc oxide
(e) 14-18% by weight of $P_2O_5$
(f) 4-7% by weight of fluoride,
and wherein the content of $Na_2O$ is less than 1% by weight.

2. The dental cement composition according to claim 1, wherein the polymerizable polyacidic polymer is obtained by a process comprising the steps of
(i) copolymerizing a mixture containing acrylic acid and one or more monomers selected from the group of maleic anhydride and itaconic anhydride, and
(ii) reacting the reaction product with HXY, wherein X and Y are as defined in claim 1.

3. The dental cement composition according to claim 2, wherein said polymerizable polyacidic polymer is obtained by copolymerizing a mixture containing acrylic acid and itaconic acid anhydride.

4. The dental cement composition according to claim 1, wherein
XY is —OCH$_2$C(=CH$_2$)COOH.

5. The dental cement composition according to claim 1, wherein the polymerizable polyacidic polymer is water-soluble.

6. The dental cement composition according to claim 1, which contains a polymerizable polyacidic polymer having repeating units represented by the formula (I) wherein a portion of the groups Y is a group of the following formula (V)

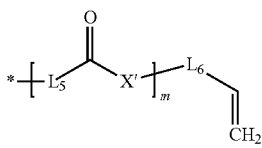

wherein
$L_5$ represents a single bond or a straight or branched $C_1$-$C_6$ alkylene group,
$L_6$ represents a straight or branched $C_1$-$C_3$ alkylene group, and
m is as defined in claim 1.

7. The dental cement composition according to claim 1, which further comprises a polymerization initiator system and optionally a polymerizable monomer having at least two polymerizable functional groups.

8. The dental cement composition according to claim 1, wherein the mean particle size of the particulate glass is in the range of from 0.1 to 100 μm.

9. The dental cement composition according to claim 1, wherein said polymerizable polyacidic polymer has a mean molecular weight, Mw, between 10000 and 500000.

10. Process for preparing a polymerizable polyacidic polymer having repeating units in the polymer backbone which are represented by the following formula (I) and/or (II):

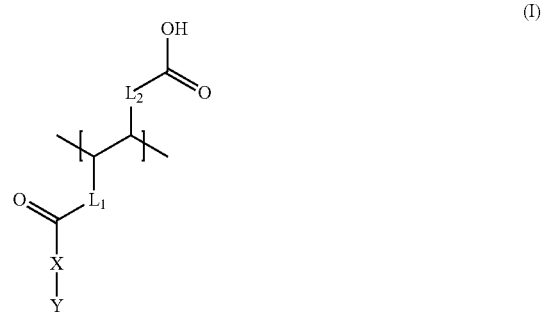

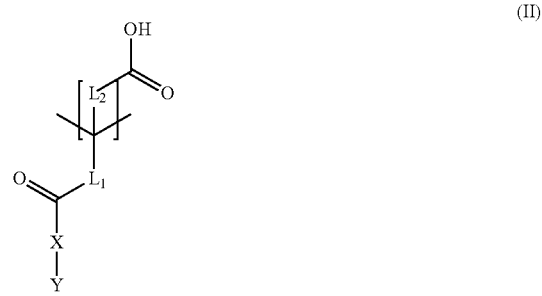

wherein
X represents O, S, or NR', whereby R' represents a hydrogen atom or a straight or branched $C_1$-$C_6$ alkyl group, $C_3$-$C_6$ cycloalkyl group, or $C_4$-$C_8$ cycloalkylalkyl group,
Y represents a group of the following formula (IV)

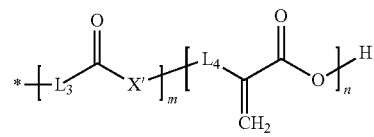

wherein each $L_1$, $L_2$, $L_3$ and $L_4$,
which are independent from each other represents a single bond, a straight or
branched $C_1$-$C_6$ alkylene group, a straight or branched $C_1$-$C_6$ alkenylene, or a straight or branched $C_1$-$C_{20}$ alkylene group which includes 1 to 8 atoms selected from oxygen and sulfur atoms, X' represents O, S, or NR", whereby R" represents a hydrogen atom or a straight or branched $C_1$-$C_6$ alkyl group, $C_3$-$C_6$ cycloalkyl group, or $C_4$-$C_8$ cycloalkylalkyl group, m is 0 to 3, and n is 1 to 3, said process comprising the steps of
  (i) copolymerizing a mixture containing acrylic acid and one or more monomers selected from the group of maleic anhydride, itaconic anhydride, and
  (ii) reacting the reaction product of (i) with HXY, wherein
    X represents O, S, or NR', whereby R' represents a hydrogen atom or a straight or branched $C_1$-$C_6$ alkyl group, $C_3$-$C_6$ cycloalkyl group, or $C_4$-$C_8$ cycloalkylalkyl group,
    Y represents a group of the following formula (IV)

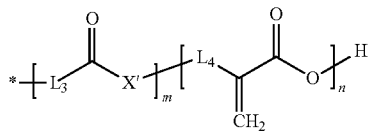

wherein each of $L_1$, $L_2$, $L_3$ and $L_4$,
  which are independent from each other represents a single bond, a straight or branched $C_1$-$C_6$ alkylene group, a straight or branched $C_1$-$C_6$ alkenylene, or a straight or branched $C_1$-$C_{20}$ alkylene group which includes 1 to 8 atoms selected from oxygen and sulfur atoms,
X' represents O, S, or NR", whereby R" represents a hydrogen atom or a straight or branched $C_1$-$C_6$ alkyl group, $C_3$-$C_6$ cycloalkyl group, or $C_4$-$C_8$ cycloalkylalkyl group,
m is 0 to 3, and
n is 1 to 3.

11. Process for preparing a polymerizable polyacidic polymer having repeating units in the polymer backbone which are represented by the following formula (III)

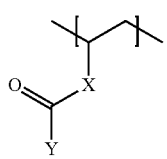

(III)

wherein
X represents O, S, or NR', whereby R' represents a hydrogen atom or a straight or branched $C_1$-$C_6$ alkyl group, $C_3$-$C_6$ cycloalkyl group, or $C_4$-$C_8$ cycloalkylalkyl group, Y represents a group of the following formula (IV)

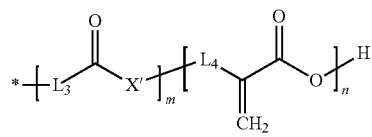

wherein each $L_3$ and $L_4$
  which are independent from each other represents a single bond, a straight or branched $C_1$-$C_6$ alkylene group, a straight or branched $C_1$-$C_6$ alkenylene, or a straight or branched $C_1$-$C_{20}$ alkylene group which includes 1 to 8 atoms selected from oxygen and sulfur atoms,
X' represents O, S, or NR", whereby R" represents a hydrogen atom or a straight or branched $C_1$-$C_6$ alkyl group, $C_3$-$C_6$ cycloalkyl group, or $C_4$-$C_8$ cycloalkylalkyl group,
m is 0 to 3, and
n is 1 to 3, said process comprising the steps of reacting a carboxylic acid anhydride of YCOOH, wherein Y represents a group of the following formula (IV)

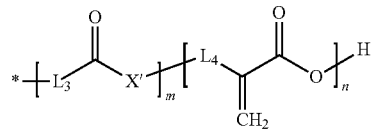

wherein each of $L_1$, $L_2$, $L_3$ and $L_4$,
  which are independent from each other represents a single bond, a straight or
  branched $C_1$-$C_6$ alkylene group, a straight or branched $C_1$-$C_6$ alkenylene, or a straight or branched $C_1$-$C_{20}$ alkylene group which includes 1 to 8 atoms selected from oxygen and sulfur atoms,
X' represents O, S, or NR", whereby R" represents a hydrogen atom or a straight or branched $C_1$-$C_6$ alkyl group, $C_3$-$C_6$ cycloalkyl group, or $C_4$-$C_8$ cycloalkylalkyl group,
m is 0 to 3, and
n is 1 to 3
with a polymer or copolymer containing repeating units of the following formula (V):

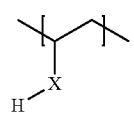

(V)

wherein X represents O, S, or NR', whereby R' represents a hydrogen atom or a straight or branched $C_1$-$C_6$ alkyl group, $C_3$-$C_6$ cycloalkyl group, or $C_4$-$C_8$ cycloalkylalkyl group.

* * * * *